US012064524B2

(12) United States Patent
Soane et al.

(10) Patent No.: US 12,064,524 B2
(45) Date of Patent: Aug. 20, 2024

(54) ABSORBENT FIBROUS COMPOSITES AND RESULTING HIGH PERFORMANCE PRODUCTS

(71) Applicant: Soane Materials LLC, Miami, FL (US)

(72) Inventors: David S. Soane, Coral Gables, FL (US); Juan Sebastian Colmenares, Reno, NV (US); Allison Greene, Reno, NV (US); Alexander Soane, Coral Gables, FL (US)

(73) Assignee: Soane Materials LLC, Miami, FL (US)

( * ) Notice: Subject to any disclaimer, the term of this patent is extended or adjusted under 35 U.S.C. 154(b) by 0 days.

(21) Appl. No.: 17/574,697

(22) Filed: Jan. 13, 2022

(65) Prior Publication Data

US 2022/0273840 A1 Sep. 1, 2022

Related U.S. Application Data

(60) Provisional application No. 63/137,411, filed on Jan. 14, 2021.

(51) Int. Cl.
| | |
|---|---|
| *A61L 15/22* | (2006.01) |
| *A61F 13/15* | (2006.01) |
| *A61L 15/42* | (2006.01) |
| *A61L 15/44* | (2006.01) |
| *A61L 15/46* | (2006.01) |
| *A61L 15/60* | (2006.01) |

(52) U.S. Cl.
CPC ...... *A61L 15/225* (2013.01); *A61F 13/15642* (2013.01); *A61L 15/425* (2013.01); *A61L 15/44* (2013.01); *A61L 15/46* (2013.01); *A61L 15/60* (2013.01); *A61L 2420/02* (2013.01)

(58) Field of Classification Search
CPC ...... A61L 15/225; A61L 15/425; A61L 15/44; A61L 15/46; A61L 15/60; A61L 2420/02; A61L 15/16; A61F 13/15642; A61F 2013/530379; A61F 2013/530386; A61F 2013/530481; A61F 13/53; A61F 13/15617

See application file for complete search history.

(56) References Cited

U.S. PATENT DOCUMENTS

| | | | | |
|---|---|---|---|---|
| 2,839,526 | A | * 6/1958 | Miller, Jr. ............... | C08B 11/20 536/86 |
| 4,065,347 | A | 12/1977 | Aberg et al. | |
| 4,081,316 | A | 3/1978 | Aberg et al. | |
| 4,443,492 | A | * 4/1984 | Roller ..................... | A61L 15/60 522/182 |
| 5,470,964 | A | 11/1995 | Qin | |
| 5,562,646 | A | * 10/1996 | Goldman ................ | A61L 15/60 428/339 |
| 5,599,335 | A | 2/1997 | Goldman et al. | |
| 5,610,220 | A | * 3/1997 | Klimmek .................. | C08F 8/44 524/556 |
| 5,611,981 | A | * 3/1997 | Phillips ............. | A61F 13/53747 264/211.14 |
| 5,801,116 | A | 9/1998 | Cottrell et al. | |
| 5,811,531 | A | 9/1998 | Iguchi et al. | |
| 5,847,031 | A | 12/1998 | Klimmek et al. | |
| 5,938,894 | A | 8/1999 | Thebrin et al. | |
| 6,059,924 | A | 5/2000 | Hoskins | |
| 6,095,996 | A | * 8/2000 | Steer ..................... | A61L 15/585 428/355 R |
| 6,162,541 | A | 12/2000 | Chou et al. | |
| 6,258,996 | B1 | * 7/2001 | Goldman ............... | A61F 13/537 604/367 |
| 6,270,845 | B1 | * 8/2001 | Pappas .................. | A61L 15/225 427/430.1 |
| 6,398,769 | B1 | * 6/2002 | Fernkvist ................ | A61L 15/28 604/370 |
| 6,479,415 | B1 | * 11/2002 | Erspamer .............. | A61F 13/534 442/385 |
| 6,632,209 | B1 | * 10/2003 | Chmielewski .... | A61F 13/49406 604/385.01 |
| 6,646,180 | B1 | * 11/2003 | Chmielewski ........ | A61F 13/539 604/382 |
| 6,824,650 | B2 | 11/2004 | Lindsay et al. | |
| 6,838,504 | B1 | * 1/2005 | Webster .................... | C22B 7/00 524/436 |
| 6,998,367 | B2 | 2/2006 | Qin | |

(Continued)

FOREIGN PATENT DOCUMENTS

| | | |
|---|---|---|
| WO | 2019158226 A1 | 8/2019 |
| WO | 2020188047 A1 | 9/2020 |
| WO | 2020226625 A1 | 11/2020 |

OTHER PUBLICATIONS

"Difference Between Sol And Gel With Examples", Retrieved from https://vivadifferences.com/difference-between-sol-and-gel-with-examples/ on Jan. 12, 2021, 3 pgs.
"What are Hydrocolloids?", Retrieved from https://www.edinformatics.com/math_science/hydrocolloids.htm on Jan. 12, 2021, 1999, 2 pgs.
Bahram, M. , et al., "An Introduction to Hydrogels and Some Recent Applications", Emerging Concepts in Analysis and Applications of Hydrogels, Retrieved at https://www.intechopen.com/books/emerging-concepts-in-analysis-and-applications-of-hydrogels/an-introduction-to-hydrogels-and-some-recent-applications on Nov. 1, 2021, 32 pgs.

(Continued)

*Primary Examiner* — Susan S Su
*Assistant Examiner* — Ted Yang
(74) *Attorney, Agent, or Firm* — Elmore Patent Law Group, P.C.; Mahreen Chaudhry Hoda; Carolyn S. Elmore

(57) ABSTRACT

The invention encompasses composite materials having a fibrous core that is at least partially covered by a water-swellable coating layer in which the water-swellable coating layer includes a water-swellable polymer. The invention also encompasses methods for manufacturing such a composite material, and further encompasses articles of manufacture made from such composite materials and methods for manufacturing such articles.

15 Claims, No Drawings

(56) References Cited

U.S. PATENT DOCUMENTS

| | | | |
|---|---|---|---|
| 7,018,945 | B2 | 3/2006 | Yahiaoui et al. |
| 7,052,775 | B2 | 5/2006 | Dohrn et al. |
| 7,407,912 | B2 | 8/2008 | Mertens et al. |
| 7,479,578 | B2 | 1/2009 | Garnier et al. |
| 7,504,551 | B2 * | 3/2009 | Herfert ............ A61L 15/60 |
| | | | 522/42 |
| 7,612,016 | B2 | 11/2009 | Mertens et al. |
| 7,625,463 | B2 | 12/2009 | Weerawarna et al. |
| 7,717,995 | B2 | 5/2010 | Weerawarna et al. |
| 7,772,420 | B2 | 8/2010 | Hermeling et al. |
| 7,794,839 | B2 | 9/2010 | Schmidt et al. |
| 8,084,391 | B2 | 12/2011 | Weerawarna |
| 8,114,809 | B2 | 2/2012 | Chevigny et al. |
| 8,236,715 | B2 | 8/2012 | Schmidt et al. |
| 8,268,424 | B1 | 9/2012 | Suzuki et al. |
| 8,450,555 | B2 | 5/2013 | Nhan et al. |
| 8,524,355 | B2 | 9/2013 | Nakaoka |
| 8,563,466 | B2 | 10/2013 | Chevigny et al. |
| 8,703,645 | B2 | 4/2014 | Tian et al. |
| 8,975,387 | B1 | 3/2015 | Venditti et al. |
| 10,729,599 | B2 | 8/2020 | Weber et al. |
| 10,842,690 | B2 | 11/2020 | Bianchi et al. |
| 2002/0000207 | A1 * | 1/2002 | Ikegami ............ A01K 1/0155 |
| | | | 119/171 |
| 2002/0007166 | A1 * | 1/2002 | Mitchell ............ B29C 48/00 |
| | | | 604/372 |
| 2003/0135172 | A1 * | 7/2003 | Whitmore ........... A61L 15/60 |
| | | | 604/359 |
| 2003/0212376 | A1 * | 11/2003 | Walter ........... A61F 13/15658 |
| | | | 442/327 |
| 2004/0157734 | A1 * | 8/2004 | Mertens ............ A61L 15/60 |
| | | | 502/401 |
| 2004/0214943 | A1 * | 10/2004 | Hager ............... C08J 7/0427 |
| | | | 524/556 |
| 2005/0013992 | A1 * | 1/2005 | Azad ................. C08J 3/243 |
| | | | 428/407 |
| 2005/0031872 | A1 * | 2/2005 | Schmidt .............. C08J 3/12 |
| | | | 428/407 |
| 2005/0033255 | A1 * | 2/2005 | Fossum ............... C08J 3/12 |
| | | | 604/370 |
| 2005/0033256 | A1 * | 2/2005 | Schmidt ............. C08J 7/056 |
| | | | 604/370 |
| 2005/0043696 | A1 * | 2/2005 | Schmidt .............. C08J 3/12 |
| | | | 604/372 |
| 2005/0215962 | A1 * | 9/2005 | Litvay .............. A61F 13/539 |
| | | | 604/358 |
| 2006/0030023 | A1 * | 2/2006 | Somers .............. C02F 3/342 |
| | | | 435/262.5 |
| 2006/0137838 | A1 * | 6/2006 | Luo ................. C08B 15/005 |
| | | | 536/56 |
| 2006/0173434 | A1 * | 8/2006 | Zoromski ........... A61F 13/53 |
| | | | 604/374 |
| 2007/0098953 | A1 * | 5/2007 | Stabelfeldt .......... A61F 13/60 |
| | | | 428/100 |
| 2007/0250024 | A1 * | 10/2007 | Mitchell ............ A61L 15/60 |
| | | | 604/372 |
| 2010/0221972 | A1 * | 9/2010 | Soane ............... D06N 7/0092 |
| | | | 427/180 |
| 2014/0121622 | A1 * | 5/2014 | Jackson ............ A61L 15/60 |
| | | | 428/401 |
| 2014/0378922 | A1 * | 12/2014 | Fuchs .............. A61F 13/42 |
| | | | 604/361 |
| 2017/0079851 | A1 * | 3/2017 | Greening, II ...... A61F 13/5633 |
| 2020/0085990 | A1 * | 3/2020 | Gao ................ A61F 13/84 |
| 2020/0121521 | A1 * | 4/2020 | Daniel ............. A61F 13/53 |
| 2021/0022931 | A1 * | 1/2021 | Chan ............. A61F 13/15203 |
| 2021/0039071 | A1 * | 2/2021 | Yoshinaga ....... B01J 20/28016 |
| 2021/0045942 | A1 * | 2/2021 | Chan .............. A61L 15/60 |
| 2021/0085536 | A1 * | 3/2021 | Isaac ............. A61F 13/511 |
| 2022/0192899 | A1 * | 6/2022 | Lee ................ B01J 20/267 |

OTHER PUBLICATIONS

Banerjee, S., et al., "Food Gels: Gelling Process and New Applications", Critical Reviews in Food Science and Nutrition, 52(4), 2012, 334-346.

Burey, P., et al., "Hydrocolloid Gel Particles: Formation, Characterization, and Application", Critical Rev in Food Sci and Nutri., 48(5), 2008, 361-377.

Choi, J. R, et al., "Recent advances in photo-crosslinkable hydrogels for biomedical applications", BioTechniques, 66 (1), Jan. 2019, 40-53.

Hennink, W. E, et al., "Novel crosslinking methods to design hydrogels", Adv Drug Del Rev., 64(Supp), Dec. 2012, 223-236.

Hu, W., et al., "Advances in crosslinking strategies of biomedical hydrogels", Biomater. Sci., 7, 2019, 843-855.

Omidian, H., et al., "Swelling agents and devices in oral drug delivery", J. Drug Del. Sci. Tech., 18(2), 2008, 83-93.

Saha, D., et al., "Hydrocolloids as thickening and gelling agents in food: a critical review", J Food Sci Technol., 47(6), 587-597, Nov.-Dec. 2010.

Schlusaz, M., et al., "Fluff pulp performance impoved by alternative pine species", Tappi Peers, Oct. 27-30, 2019, St. Louis, MO.

Sigma-Aldrich, "Water-Swellable Polymer Networks From Hydrogels to Superabsorbers", https://www.sigmaaldrich.com, 1 pg.

Thakur, B. R, et al., "Chemistry and uses of pectin—A review", Critical Reviews in Food Science and Nutrition, 37(1), 1997, 47-73.

* cited by examiner

ABSORBENT FIBROUS COMPOSITES AND RESULTING HIGH PERFORMANCE PRODUCTS

RELATED APPLICATION

This application claims the benefit of U.S. Provisional Application Ser. No. 63/137,411, filed Jan. 14, 2021. The entire contents of the above application are incorporated by reference herein.

FIELD OF THE APPLICATION

This application relates to absorbent fiber-based composites, and articles formed therefrom.

BACKGROUND

Fibrous composite products are useful for many applications. As an example, disposable absorbent articles employed as personal care products, are formed from cellulose fibers in combination with superabsorbent polymer materials, which allow the product to absorb and manage large volumes of fluids such as bodily excretions. In these disposable absorbent articles, such as diapers, adult incontinence products, feminine hygiene products, and the like, the working component is an absorbent structure comprising a fibrous core such as debonded fluff-pulp that bears superabsorbent polymer (SAP) gel beads or other particulate absorbent materials. There are inherent limitations to such absorbent articles however, stemming from the composite construction using a fibrous support and a polymeric superabsorbent component attached thereto.

The fluff pulp fibers used as the core of absorbent articles provide mechanical strength and integrity to this layer when it is incorporated within the finished product. However, fluff pulp fibers within the composite structure of an absorbent article can become stiff and rigid, so that the article conforms poorly to the contours of the wearer. Besides providing strength and structural support, the fluff pulp fibers in the absorbent composite product allow for the distribution of fluids within the structure, allowing the absorbent particulates to absorb it evenly. The properties of the SAP particulates in the composite can work at cross-purposes with this goal. The principal function of the absorbent mixed layer of debonded fluff pulp and particulate absorbents is fluid retention, which also involves fluid distribution to alleviate performance demand. However, with this fiber-particulate composite approach, poor absorption is not simply a capacity issue: it is also a matching problem between absorption speed/capacity of SAP and the degree/rate of liquid spreading to other parts of the absorbent pad.

Liquid spreading throughout the absorbent layer constructed using conventional technologies is facilitated by the porosity (void volume fraction) of this layer, which is supported by the spaced-apart matrix of the fluff pulp fibers. However, the absorbent behavior of the SAP beads in this layer interferes with liquid diffusion. As the SAP beads swell, they impinge upon the adjacent pores, diminishing the local pore volume at the point of liquid introduction and thereby decreasing the permeability of the absorbent article and impeding fluid spreading. Under these circumstances, only a small portion of the absorbent article remains available for diffusing the fluid load after fluid is introduced, so that the localized site of liquid injection must bear the entire liquid assault.

In more detail, the initial structural density of the mixed core of a typical absorbent article like a diaper or adult incontinence pad is about 0.3 g/cc, corresponding to a void fraction about 80%, (i.e., 80% of the volume in the structure could in principle be occupied by liquid). When liquid is first introduced into the article, the void space near the injection point is quickly filled, and additional liquid that continues at the injection site must wait for these liquid-filled spaces to be emptied before being accepted by the product without side leakage. There are two mechanisms to handle the extra liquid: (1) spreading it along the inter-connected void space to the peripheral structure, and (2) absorbing it in the SAP beads. Unfortunately, conventional fiber-based products that use SAP beads exhibit gel blocking (or gel clogging) behavior, attributable to the softness of the SAP beads, their discrete geometrical shape, and the pressure of the product in the use environment. Gel blocking occurs when SAP beads become engorged and enlarged after absorbing a certain amount of liquid, following which they deform, shift, and clump onto each other, blocking voids in the fibrous matrix and inhibiting further transmission of liquid to other parts of the absorbent article.

These features of SAP behavior can be counteracted in part by crosslinking techniques. SAPs useful for forming absorptive beads are often made by polymerizing unsaturated carboxylic acids or derivatives thereof and crosslinking these polymer chains (for example, crosslinked polyacrylate) to make an absorbent material that is water-insoluble but water-absorbing (i.e., hydrogel-forming). Increasing the amount of crosslinking can increase the gel strength of the liquid-saturated absorptive beads, while typically also reducing their absorptive capacity. Increasing the gel strength of the hydrogel layer improves its permeability by retaining structural integrity in this layer and decreasing gel blockage, but the increase in permeability produced by the crosslinking comes at the expense of absorbent capacity. In other words, while crosslinking provides stability and strength to the absorptive article, it decreases absorption, so that the article requires a higher dosage of SAP beads to provide sufficient overall absorption. Increasing the dosage of SAP beads in the article, however, can affect its structural integrity when it is saturated with liquid. Moreover, expensive and difficult fixation technologies are required to hold the SAP beads in place within the article itself, leading to SAP bead loss during the processes used to form the article.

An additional layer of crosslinking can be formed on the surface of the SAPs themselves as the SAP beads are incorporated into the fibrous mesh, resulting in improved SAP properties in specific absorbent articles. Surface crosslinking for SAP beads has its own limitations, however. Surface crosslinking can constrain the absorption capacity of the SAP particles because their ability to swell is physically restricted, preventing them from absorbing their full capacity of liquid. Surface crosslinking is designed to be relatively weak so that it does not constrain bead swelling, but as a consequence the crosslinks might not have sufficient strength to withstand the stresses of swelling or the stresses associated with load bearing when the article is being worn. As a result, the crosslinked coating layer can fracture as the polymer swells initially or after the polymer has been in a swollen state for a period of time. With the fracture of the coating layer, the SAP materials can deform, resulting in a decrease in porosity and permeability, with liquid trapped in this layer that cannot be wicked away from the wearer's skin surface.

Furthermore, the restrictions imposed by crosslinking compromise the biodegradability of the absorbent article, because the lower permeability of the SAP layer reduces the ability of microorganisms to invade this layer and decompose it. In addition, various chemical components introduced into the SAP layer, for example to enhance surface crosslinking of the beads, can inhibit microbial activity and/or enzymatic degradation. Moreover, the current leading SAP is crosslinked polyacrylate, a petroleum-derived material that is not biodegradable. All of these characteristics of conventional disposable absorbent articles contribute to a looming landfill problem.

As an additional problem, while the air-laying process is familiar in the industry for forming absorbent pulp-bead composites, this process is also an inefficient one for producing these structures, because a portion of the SAP beads fail to become physically entrapped by the fiber matrix. This inefficiency adds costs to the process, and can require complex work-arounds.

While personal care articles such as diapers, adult incontinence products, feminine hygiene products, pet training pads, and the like using SAP technology have achieved wide commercial success despite their limitations, there are other products that have not been successful in employing SAP technology to improve their absorbency. In particular, thin paper products like paper towels and tissue paper rely on high absorbency and fluid spreading, but they are designed to prioritize their thin dimensional profile despite fluid exposure. For many such applications, improved absorbency and wet strength would be desirable. However, since these products are designed to be thin under use conditions rather than swellable, SAP beads (which increase in volume with fluid absorption) are not suitable for improving their absorbent performance.

There remains a need in the art, therefore, for an improved architecture for absorbent articles that improves structural integrity while optimizing fluid uptake and maintaining porosity for wicking and breathability of the absorbent layer. There is additionally a need for a more efficient process that adds a material with absorbent properties to a fibrous core. There is also a need for a biodegradable or compostable absorbent article that can be disposed of responsibly. Furthermore, it is desirable that an absorptive technology can be used in a thin-sheet form to offer improved absorption and enhanced wet strength while allowing the article to retain its thin-sheet profile.

SUMMARY

Disclosed herein, in embodiments, are composite materials comprising a fibrous core at least partially covered by a water-swellable coating layer, wherein the water-swellable coating layer comprises a first water-swellable polymer. In embodiments, the fibrous core comprises a cellulosic material or consists essentially of the cellulosic material, and the cellulosic material can be a fluff pulp. In embodiments, the water-swellable coating layer comprises a second water-swellable polymer, and the first water-swellable polymer can be a carboxyalkyl cellulose, and the second water-swellable polymer can be xanthan gum. In embodiments, the first water-swellable polymer and the second water-swellable polymer are organized in a heterogenous polymer network formed by charge-charge complexation. In embodiments, the water-swellable coating layer comprises a foam, which can be sustained or formed by a foam-producing material. The foam-producing material can comprise a surfactant. In embodiments, the water-swellable coating layer comprises one or more additives not having water-swellable properties, which can be selected from the group consisting of plasticizers, skin rejuvenating agents, medications, odor absorbers or neutralizers, and fragrances. In embodiments, the additive is a plasticizer. In other embodiments, the additive is a strengthening additive, which can comprise natural insoluble fibrous materials and/or nanocellular elements. In embodiments, the water-swellable polymer can be a synthetic water-swellable polymer, or it can be a naturally-derived water-swellable polymeric material. In embodiments, such a naturally-derived water-swellable polymeric material can comprise a naturally-derived hydrocolloid, which can be a polysaccharide. Such polysaccharides can be selected from the group consisting of as xanthan gum, pectin, amylopectin, carrageenan, alginate, agar-agar, cellulose gum, celluloses, pectin ester, gellan gum, guar gum, gum Arabic, locust bean gum, diutan, welan, tarn, olibanum, karaya, ghatti, dammar, tragacanth gum, and derivatives thereof. In embodiments, the polysaccharide can be xanthan gum or a cellulose; the cellulose can be a carboxyalkyl cellulose, which can be selected from the group consisting of carboxymethylcellulose, hydroxyethyl cellulose, and carboxymethyl hydroxyethyl cellulose. In embodiments, the composite material comprises a second naturally derived hydrocolloid, which can be xanthan gum. In embodiments, the water-swellable polymer forms a hydrogel upon contact with water. In embodiments, the water-swellable polymer is crosslinked, and it can be crosslinked only on its surface. In embodiments, crosslinking is performed by a crosslinker, or by a crosslinker and an additional crosslinking agent. The crosslinker and the additional crosslinking agent can have different properties; the additional crosslinking agent can be a catalyst. In embodiments, the crosslinker is a bulky and slow-diffusing crosslinking agent; in embodiments, the crosslinker is a multifunctional epoxy with oligomeric arms; in embodiments, the crosslinker is selected from the group consisting of citric acid, butanetetracarboxylic acid, poly (methyl vinyl ether-alt-maleic anhydride), polymeric methylene diphenyl isocyanate, poly(ethylene glycol) and diglycidyl ether.

Also disclosed here, in embodiments, are articles of manufacture comprising the composite material as described above. In embodiments, such an article of manufacture can be a personal care product, which can be selected from the group consisting of diapers, adult incontinence products, fluid absorption pads, and feminine hygiene products. In embodiments, such an article of manufacture can be a medical use product intended for a medical use, and the medical use can be selected from the group consisting of wound treatment, blood coagulation, treatment of a skin condition, surface application of a medical or wellness treatment, and transdermal dissemination of a pharmaceutical treatment.

Further disclosed herein are methods of manufacturing the composite materials as described above. Such methods can include the steps of providing a cellulosic substrate in dry or slightly wet form; mixing the cellulosic substrate with an aqueous suspension of a water-swellable polymer to form a coating mixture; applying the coating mixture to the cellulosic substrate to form a coated cellulosic substrate having a substantially uniform coating of the water-swellable polymer on the cellulosic substrate; and forming the coated cellulosic substrate into a sheet. In embodiments, the cellulosic substrate is a fluff pulp. In embodiments, the step of mixing utilizes an industrial mixer or an extruder; the step of mixing can further comprise a substep of expanding the coating mixture by foaming. In embodiments, the step of forming utilizes a calendar roll, a blade coater, or a slit dye. in embodiments, the methods can further comprise a step of applying a crosslinker formulation to the sheet substantially evenly, whereby the crosslinker formulation reaches at least the surface of the substantially uniform coating and effects crosslinking thereof. In embodiments, the step of applying the crosslinker formulation utilizes a spray bar to spray the crosslinker formulation uniformly across the sheet. In embodiments, the step of applying the crosslinker formulation employs a pressure differential to distribute the crosslinker formulation throughout the sheet substantially evenly. in embodiments, the crosslinker formulation acts only on the surface of the substantially uniform coating; in other embodiments, the crosslinker formulation penetrates the surface to effect crosslinking of a portion of the substantially uniform coating beneath the surface.

In addition, methods are disclosed herein for forming an absorbent article, comprising the steps of providing the composite material described above; treating the composite material with a mechanical separation process to increase interfiber separation; drying the composite material before or after the step of treating, thereby forming a dried absorbent fibrous product; and cutting the dried absorbent fibrous product into a shape suitable for the absorbent article. In embodiments, the fibrous core of the composite material comprises cellulosic material, which can be fluff pulp and the mechanical separation process can be a hammermill process.

DETAILED DESCRIPTION

1. Component Structures for Absorbent Fibrous Composites
a. Fibers as Core Materials Disclosed herein are absorbent composites comprising a fibrous core and a coating comprising a water-swellable polymer. In embodiments, the fibrous core can be formed from a naturally-sourced and biodegradable material. As used herein, the term "fiber" refers to a structure having a large aspect ratio (i.e., a dimensional length much larger than its cross-sectional dimension, for example an aspect ratio that is larger than about 10, 20, 30, 50, or 100). "Fibrous" as an adjective describes a substance that comprises fibers. As used herein, the term "natural" as a modifier for the term "fiber" refers to a fiber derived from a natural source. Natural and naturally-derived fibers include vegetable-derived fibers, animal-derived fibers and mineral-derived fibers. Vegetable-derived fibers can be predominately cellulosic, e.g., wood pulp, cotton, jute, flax, hemp, sisal, ramie, and the like. Naturally derived vegetable-derived fibers can include fibers such as cellulose that are chemically modified: for example, cellulose (a natural material) can be modified to form other cellulose-based naturally-derived fibers such as Rayon® or Lyocell®, or cellulose acetate fibers. Vegetable-derived fibers can include fibers derived from seeds or seed cases, such as cotton or kapok, or fibers derived from leaves, such as sisal and agave, or fibers derived from the skin or bast surrounding the stem of a plant, such as flax, jute, kenaf, hemp, ramie, rattan, soybean fibers, vine fibers, and banana fibers, or derived from the fruit of a plant, such as coconut fibers, or derived from the stalk of a plant, such as wheat, rice, barley, bamboo, and grass. Vegetable-derived fibers can include wood fibers or wood pulp fibers. Animal-derived fibers typically comprise proteins, e.g., wool, silk, mohair, and the like. Mineral-derived natural fibers are obtained from minerals. Mineral-derived fibers can be derived from asbestos. Mineral-derived fibers can be a glass or ceramic fiber, e.g., glass wool fibers, quartz fibers, aluminum oxide, silicon carbide, boron carbide, and the like. Synthetic fibers are formed from synthetic (manufactured, not naturally derived) materials that are inorganic or organic. Synthetic inorganic fibers include manufactured mineral-based fibers such as glass fibers and metallic fibers. Glass fibers include fiberglass and various optical fibers. Metallic fibers can be deposited from brittle metals like nickel, aluminum or iron, or can be drawn or extruded from ductile metals like copper and precious metals. Synthetic organic fibers include fibers manufactured from polymeric materials such as polyamide nylon, PET or PBT polyester, polyesters, phenol-formaldehyde (PF), polyvinyl alcohol, polyvinyl chloride, polyolefins, acrylics, aromatics, polyurethanes, elastomers, and the like. A fiber can include one or more types of component fibers, whether natural or synthetic. For example, a synthetic fiber can be a coextruded fiber, with two or more synthetic polymers forming the fiber coaxially or collinearly.

b. Fibrous Cellulosic Core

In exemplary embodiments, the fibrous core for the absorbent fibrous composite comprises or consists of a cellulosic core. Cellulose and cellulosics as core materials are particularly advantageous for the formation of absorbent articles, as described in more detail below. In embodiments, the fibrous cellulosic core is produced using techniques familiar in the papermaking industry, for example, techniques for forming debonded fluff pulp.

As used herein, the term "cellulosic" is meant to include any material having cellulose as a major constituent, for example those materials comprising at least 50 percent by weight of cellulose or of a cellulose derivative. Thus, the term "cellulosic" includes typical wood pulps, nonwoody cellulosic fibers, cellulose acetate, cellulose triacetate, rayon, mechanical wood pulp, thermomechanical wood pulp, chemical wood pulp, debonded chemical wood pulp, milkweed, bacterial cellulose, cotton, and recycled materials derived from the foregoing. In embodiments, non-wood fibers or mechanical wood pulp fibers can be present, for example in amounts less than about 40% by weight of the dry pulp fiber weight used for the cellulosic cores, or less than about 30% by weight, or less than about 20% by weight, or less than about 10% by weight. Additional fibers can be added to the cellulosic core from a variety of other fiber sources as described above. In embodiments, natural fibers such as bagasse, bamboo, corn, cotton, flax, hemp, kenaf, peat moss, silk, and the like can be added, and/or synthetic fibers such as acrylic, carboxylated polyolefins, nylon, polyester, rayon, and the like.

In an exemplary embodiment, the fibrous cellulosic material used as the core of the absorbent fibrous composite can be derived from debonded fluff pulp. Fluff pulp is formed by first chemically separating cellulose fibers from the other components of wood, or other the other components of cellulose-containing materials such as fiber crops or sources of recycled cellulose such as recycled paper, cardboard, and the like. Chemical pulping such as the Kraft process or sulfite process degrades the lignin and hemicellulose in wood or other plant materials into small, water-soluble molecules that can be rinsed off of the cellulose fibers without depolymerizing the cellulose. The resulting pulp is a lignocellulosic material that can then be formed as a uniform sheet or non-woven mat on a simplified Fourdrinier machine, with debonders added before drying to facilitate the subsequent defibration. To form fluff (or fluffed) pulp, the chemically debonded sheets are subjected to mechanical defibration, for example in a hammermill, yielding a dry defibrated product that can be used to form absorbent articles. Techniques for forming fluff pulp are familiar in the art, for example as described in U.S. Pat. Nos. 6,059,924, 4,081,316, and 4,065,347, the disclosures of which are incorporated herein by reference.

Wood fibers advantageous for use in making dried fluff pulp are generally derived from softwoods (gymnosperms) such as pine, Douglas fir, spruce, and hemlock, which are long-fiber coniferous wood species; exemplary species include *Picea glauca* (white spruce), *Picea mariana* (black spruce), *Picea rubra* (red spruce), *Pinus strobus* (white pine), *Pinus caribeau* (slash pine), and *Pinus tadea* (loblolly pine). While softwood materials are commonly used for fluff pulp, the absorbent fibrous composite materials disclosed herein can additionally or alternatively contain fluff pulp made from hardwood (angiosperm) fiber sources such as alder, aspen, gum (for example, *eucalyptus*), oak, and the like. In embodiments, the fluff pulp can be derived from one or more wood sources, including mixtures of softwoods, hardwoods, or both. Wood pulp fibers for forming these cellulosic cores can be prepared from any pulping process, including mechanical pulping techniques such as thermo-mechanical, chemimechanical, and chemithermomechanical pulp processes.

c. Water-Swellable Coating Materials

In embodiments, a water-swellable coating or shell is formed that covers the cellulosic core partially or completely. In embodiments, a relatively complete coverage of the cellulosic core by the water-swellable coating or shell is desirable, because larger quantities of water-swellable material on the surface of the fibers can produce advantageous properties for the composite.

Materials used to form water-swellable coatings or shells for the composites disclosed herein can include natural or synthetic hydrophilic polymers that absorb significant amounts of water or aqueous fluids in a relatively short period of time. In other words, such polymers are water-swellable, (i.e., absorbing significant amounts of water or aqueous fluids in a relatively short period of time) and are said to have water-swellable properties. A water-swellable polymer can be deployed as a solid dispersed in a liquid phase, forming a sol (i.e., a colloidal suspension of very small solid particles in a continuous liquid medium); a water-swellable polymer can also imbibe water and form a hydrophilic polymer network that ensnares the liquid within the network through surface-tension effects and hydrogen bonding, thus forming a colloidal suspension that is viscous enough to behave like a solid (i.e., a gel). Instead of dissolving in the presence of water, a water-swellable polymer soaks up the water, complexes with it, or otherwise binds to it to form a three-dimensional network. Hydrophilic groups on the polymers can account for the avid hydrophilicity of a water-swellable polymeric network.

Water-swellable polymeric networks may range from being mildly absorbing, typically retaining 30 wt. % of water within their structure, to superabsorbing, where they retain many times their weight of aqueous fluids. When they form into a stable three-dimensional gel structure, this structure is termed a hydrogel: as used herein, the term "hydrogel" refers to a relatively water-insoluble gel that is formed from inclusion of water within a matrix of water-swellable materials. Certain hydrogels can be formed from cross-linked or entangled networks of linear homopolymers, linear copolymers, or block or graft copolymers. Other hydrogels can be formed as interpenetrating networks, physical blends, or hydrophilic networks stabilized by hydrophobic domains. In other instances, hydrogels can be formed as polyion-multivalent ion complexes, or polyion-polyion complexes, or hydrogen-bonded complexes. Hydrogels can be reversible (physical) hydrogels or permanent (chemical) hydrogels. Physical hydrogels include: simple entanglement systems, in which the water-containing polymeric network is held together by molecular entanglements or crystallites; ion-mediated networks, in which the network is stabilized by interaction between oppositely charged polyelectrolyte and multivalent ions; and thermally induced networks that form three-dimensional structures in response to heating or cooling. Chemical hydrogels are mainly supported by covalent bonds, including bonded structures like cross-linked polymers or copolymers, or polymerized inter-penetrating networks. Hydrogels can also be formed by crosslinking or entanglements that take place in response to external stimuli, including application of light and changes in temperature. Light stimulus is especially advantageous for crosslinking applications because its delivery is easy to regulate and quantify. Lights can be switched on and off, allowing the dose to be controlled precisely to achieve the desired functional effects. Moreover, light wavelength can be selected specifically to produce desired properties in the resultant hydrogel. Ultraviolet light exposure is advantageous, while other wavelengths can be selected as appropriate.

Water-swellable polymers and the hydrogels that they form can be natural materials or synthetic, or combinations thereof. For example, natural water-swellable polymers include anionic polymers like alginate and carrageenan, cationic polymers like chitosan, and neutral polymers like dextran, agarose, cellulose, and their derivatives. Synthetic water-swellable polymers include polyesters like PEG and PLA, acrylates, and polyvinyl alcohol.

In embodiments, the water-swellable polymeric materials used to form the coating or shell of the fibrous core can comprise naturally-derived hydrocolloids that comprise high molecular weight hydrophilic polymers whose polar or charged functional groups render them soluble in water and further impart water-swellable properties. An important class of naturally-derived hydrocolloids for forming the composites disclosed herein are polysaccharides, which have additional advantages of biodegradability and well-recognized, regulatory-friendly acceptance for personal care and other health and wellness applications. Examples of water-swellable polysaccharides useful for forming the composites disclosed herein include materials such as xanthan gum, pectin, amylopectin, carrageenan (or including without limitation kappa, iota or lambda carrageenans), alginate and alginates (including without limitation derivatives such as propylene glycol alginate), agar-agar, cellulose gum, celluloses (such as carboxyalkyl celluloses, including but not limited to carboxymethylcellulose, hydroxyethyl cellulose, carboxymethyl hydroxyethyl cellulose and the like), pectin ester, gums such as gellan gum, guar gum and guar derivatives, gum Arabic, locust bean gum, diutan, welan, tarn, olibanum, karaya, ghatti, dammar, tragacanth gum, or modifications or mixtures of any of the foregoing. In embodiments, high viscosity polysaccharides are especially advantageous for their swellable properties. Other desirable biopolymers for use alone or with the aforesaid water-swellable polysaccharides can include starch, modified starches, amylose, modified amylose, chitosan, modified chitosan, chitin, modified chitin, gelatin, konjac, modified konjac, fenugreek gum, modified fenugreek gum, mesquite gum, modified mesquite gum, aloe mannans, modified aloe mannans, oxidized polysaccharides, sulfated polysaccharides, cationic polysaccharides, and the like. In embodiments, a synthetic water-swellable polymer (for example, polyacrylate or polyacrylamide) can be combined with any of the foregoing, or can be used as an alternative to a naturally-derived water-swellable polymer.

Xanthan gum (XG) is a natural hydrocolloid that is especially advantageous as a coating material for the fibrous cores disclosed herein. XG is an anionic polysaccharide resistant to a broad range of changes in temperature, pH, and salinity. XG can form rigid helical structures due to the availability of hydrogen bonds between its trisaccharide sidechains and its polymer backbone. Consequently, the randomized spatial orientation of these rigid helices renders them capable of high swelling performance when crosslinked. Due to this robust swelling mechanism, a single low polymer add-on (<1.5 wt % LOI) coated onto the core fibrous substrate can form a gel capable of taking up 10 to 1000 times its weight in liquids, or even more. Polysaccharide polymers that are capable of taking up at least 50 times, at least 100 times, at least 300 times, at least 500 times, at least 800 times, at least 900 times, or at least 1000 times their weight in water are particularly useful. In embodiments, the amount of such an absorbent polymer (on a dry solids basis) that is applied to the substrate can generally be between about 0.1-10 wt. %, or between 0.5-5 wt. % based on the weight of the substrate material. Within these broad ranges, polymer loadings of <5 wt. %, <4 wt. %, <3 wt. %<2 wt. %, and even <1.5 wt. % can be advantageous.

While water-swellable polymers such as those disclosed above are advantageous for preparing formulations for coating fluff pulp, it is recognized that some of these polymers (e.g., cellulose polymers such as hydroxyethylcellulose) are expensive or available only in limited amounts. Decreasing the volume of polymeric coating material used for preparing coated fluff pulp composites can therefore make these materials more cost-competitive with conventional absorbent materials such as SAPs and can provide improved performance, such as increased swelling. To achieve this, the polymer mixture can be expanded by foaming before it is applied to the fluff pulp matrix. A number of different foaming technologies can be applied to the polymeric mixture to expand its volume, for example adding materials that produce foams and/or that sustain foams within the polymer mixture (either, a "foaming material"). In an embodiment, $CO_2$ bubbles can be produced in the mixture by carrying out appropriate chemical reactions within the mixture itself; for example, an acid-carbonate neutralization reaction can be carried out, using a foam-producing material such as sodium bicarbonate and an acid such as citric acid. The bicarbonate particles can be added to the polymer mixture as a foam-producing material, followed by the addition of the acid, yielding gaseous carbon dioxide. The $CO_2$ bubbles thus produced in the mixture can then be agitated within the mixture to form the foam. The voids formed by the $CO_2$ bubbles within such a foam range from nanoscale to a size visible to the naked eye, introducing a high level of porosity with the desired expansion of volume. As another approach to foaming, mechanical methods can be used, as are familiar in the art, for example through the use of high-speed overhead mixers or immersion blenders.

In embodiments, surfactants can be added to the swellable polymer mixture as a final ingredient. The presence of surfactants can facilitate foaming through mechanical or chemical means. Adding a surfactant also can reduce the amount of swellable polymer needed in a given volume of the mixture. Without being bound by theory, it is understood that a surfactant can have the effect of creating microvoids within the swellable polymer mixture, where bubbles (later allowing the formation of nano- or microvoids) are formed from the surfactants themselves as the hydrophobic and hydrophilic segments of the surfactant molecules align into hollow spheres or other shapes, such as hexagonal prisms; randomly distributed, these microvoids can allow the entry of water molecules into the swellable polymer network, increasing its ability to swell. This effect on swellability complements the effect that the surfactant can have on facilitating foaming, and thus reducing the amount of polymer needed for an effective swellable coating on the fluff pulp. To facilitate foaming, surfactant can be added to the base formulation (such as has been described herein) in ratios ranging from about 90/10 (polymer to surfactant) to about 50/50, with those ranges having higher amounts of surfactant being more effective for producing foam and for producing swellability of the final mixture as applied to the fluff pulp matrix. Examples of surfactants useful for these purposes include capryl glucoside, coco glucoside, sodium dodecyl sulfate, and the like, in particular surfactants that are familiar to artisans in the personal care industry. In embodiments, the surfactants can be introduced into the mixture as a final step before drying to avoid premature foaming of the formulation and to facilitate the foaming of the completed mixture, including any additives. After the surfactant is added, foaming can be carried out, using methods familiar in the art for producing foam mechanically or chemically. Following foaming, a mixture is produced having little transparency, attributable to the foam bubbles distributed throughout. The material, after being dried, was tested for absorbency and was observed to yield a swellability of 28-32 times its dry weight, a result that is comparable to or better than what is currently available using conventional SAPs.

In embodiments, other additives can be included in the water-swellable coating formulation to improve performance. For example, the addition of glycerin/glycerol or similar compounds to the formulation can improve performance, decrease flaking of the coating, and the like. Glycerin/glycerol may be added in small amounts, for example, in an amount between about 0% to about 20%, or between about 5% and about 15%, or between about 9% and about 12%. As an example, glycerin or glycerol can be added to a XG formulation in an amount of about 10%: a coating formulation comprising 10% XG polymer and 1% glycerin or glycerol can improve swelling performance and improve coating consistency with reduced flakiness and enhanced ductility.

As another example, a particulate solid material can be added to the water-swellable coating in order to impart specific features to the final product. Solids such as activated charcoal, activated carbon, biochar, and the like can be included in the coating and thus can become embedded in the fluff pulp composite, enabling the composite material to capture odor-causing molecules. This ability to reduce odors is particularly advantageous for fluff pulp products used in personal care items, diapers, and the like. Such solids can further increase the strength of the composite material due to the mechanisms described below.

In advantageous embodiments, strengthening additives such as fibers or particles can be included in the water-swellable coating to improve the overall performance of the composite fluff-pulp-based material as described herein. It is understood that applying a thicker layer of the swellable polymer coating formulation to the pulp matrix can improve the overall strength of the composite, but the additional polymer increases the likelihood that the voids within the matrix will be blocked, with a consequent impact on swellability and absorbency. Without being bound by theory, it is envisioned that the fibers or particles selected for strengthening purposes can reinforce the fluff pulp matrix by filling in pores within the pulp fibers, thereby increasing the strength of the overall composite. Small fibers or particles can fill in, or block, the pores so that movement within the coated fluff pulp composite is restricted, and they can add to the amount of material per cross sectional unit, thereby increasing the overall strength of the final composite product. In addition, it is also envisioned that the fibers or particles can interact with the polymer itself, such that the fibers or particles constitute a dispersed phase within the polymeric matrix, thereby forming a multiphase material of increased strength for application to the fluff pulp matrix. Using fibers or particles, the strength of the water-swellable coating itself is improved. Thus, there are thus two separate mechanisms at work for improving the properties of the overall composite: 1) filling the pores within the fluff pulp to improve absorbency and strength, and 2) preparing the water-swellable coating formulation as a multiphase composite having increased strength, and using it to coat the fluff pulp fibers. Using these two mechanisms (pore filling and fiber coating), the fibrous or particulate additives can be used to improve the strength of the overall fluff pulp composite (i.e., the polymer-coated fluff pulp matrix), including without limitation increased tensile, compressive, shear, or torsional strength.

Strengthening additives can be selected based on the particular properties of concern in the finished composite material. Advantageously, fibers or particles that are relatively insoluble in water or urine can be used. In embodiments, natural insoluble fibrous materials such as chitosan fibers, alginate fibers, seed fibers, leaf fibers, bast fibers, fruit fibers, stalk fibers, animal fibers, collagen, and the like, can be used. In other embodiments, small insoluble organic or inorganic particles can be used, such as *psyllium* husk powder, walnut shell granules, precipitated calcium carbonate, zinc oxide, titanium dioxide, and the like.

In embodiments, natural insoluble materials such as nanofibrillated cellulose, microfibrillated cellulose, or crystalline cellulose particles (collectively, "nanocellulosic elements" or "NCEs") can be added to the swellable polymer coating formulation to improve its strength and other properties. NCE strength additives are particularly desirable because they are derived from plant-based cellulosic materials and thus do not detract from the favorable environmental profile of the coated fluff pulp composites disclosed herein. Sources for NCEs include, without limitation: virgin biomass, as is found naturally occurring plants like trees, bushes, and grass; waste products from agriculture such as corn stover and corncobs, sugarcane bagasse, straw, oil palm empty fruit bunch, pineapple leaf, apple stem, coir fiber, mulberry bark, rice hulls, bean hulls, soybean hulls (or "soyhulls"), cotton linters, blue agave waste, North African glass, banana pseudo stem residue, groundnut shells, pistachio nut shells, grape pomace, shea nut shell, passion fruit peels, fique fiber waste, sago seed shells, kelp waste, juncus plant stems, and the like; waste products from forestry, including discards from sawmills and paper mills; and special-purpose crops such as switchgrass and elephant grass that are cultivated for uses such as biofuels.

As used herein, the term "nanofibrillated cellulose" (NFC) and "microfibrillated cellulose" (MFC) refer to elongated cellulose fibrils that are extracted from plant-derived cellulosic raw materials. NFC fibers and MFC fibers differ from each other in size and shape: NFC fibers are much smaller in diameter than MFC fibers, and can be straight and rod-like; MFC fibers are larger in diameter, more flexible in appearance and can be irregular in shape. While the literature cites a range of dimensions for NFC fibers and MFC fibers, NFC fibers are nanoscale (for example, having a diameter between 10-20 nm), while MFC fibers can be much larger, but with diameters that are still in the nano-range, for example 20-100 nm. As used herein, the term "crystalline cellulose" refers to cellulosic particulate matter derived from the crystalline regions of cellulose chains in plant-derived cellulosic raw materials. Crystalline cellulose can be extracted in particulate form, yielding products that are termed cellulose nanocrystals or cellulose microcrystals, depending on the size of the particles.

In an embodiment, a NCE such as NFC fibers can be mixed into a swellable polymer formulation. NFC fibers in amounts of 0.1% (dry) and 0.05% (dry) have been tested, showing that some swellability of the polymeric mixture was retained while the strength of the coated fluff pulp product was improved. In certain experiments, adding less of the NFC fiber additive preserved more swellability. In other embodiments, strengthening the composite cellulosic product can be accomplished by using stronger pulp stocks for the pulp matrix. Hardwood pulp can provide a stronger pulp matrix than softwood pulp, for example, and the hardwood pulp fluff pulp can be used alone or in combination with other pulp matrices; other tree-free pulps such as bagasse produce strong pulp matrices as well, and can be used alone or in combination with other pulps to improve overall matrix strength. Use of stronger fluff pulp matrices can be combined with reinforcing the swellable polymer coating with fibers or particles as described above.

d. Applying the coating to the fibrous core matrix

To apply the selected water-swellable polymer to the fibrous core of the composite cellulosic product, an aqueous solution is first prepared from the chosen water-swellable polymer and mixed with dry (or slightly wet) pulp fiber at a stoichiometric ratio that provides appropriate coverage of the fibers upon drying, for example at a ratio of about 1 wt. % of aqueous xanthan to dry pulp, or 1%, 2% or 3% dry xanthan to dry pulp. Higher loadings of the water-swellable polymer lead to more viscous coating solutions with thicker resulting films on pulp surface.

In embodiments, additives can be employed to better control the deposition of the swellable polymers on the fluff pulp fibers within the fluff pulp matrix. In certain cases, the selected swellable polymer can not only coat the pulp fibers but can also occupy and clog the pores within the overall fluff pulp matrix, leading to performance problems. It is understood that leaving voids or pores open within the fluff pulp matrix encourages overall swelling of the material, while clogging the voids or pores can prevent the desirable swelling. To address this problem and facilitate swelling, the selected swellable polymer can be mixed with an additive such as an alcohol, an acetone, or a similar solvent in which the polymer itself is not soluble; the use of such additives can predispose the polymer to deposit itself directly onto the fluff pulp fibers without infiltrating the pores to clog them. To employ such a solvent in this way, it can be added to the pulp slurry before or after the swellable polymer is added. For example, the swellable polymer can be added as an aqueous solution before or after a small amount of the solvent is added (e.g., an amount of solvent less than about 10%, based on swellable polymer weight) to form a polymer-solvent mixture. If fibrous or particulate additives are to be used for increased strength, they can be added at this stage as well. The mixture, containing any desirable additives along with the swellable polymer, can then be applied to the pulp matrix. While it can be advantageous to deposit the swellable polymer selectively on the pulp fibers as described above, thereby preventing the polymer from clogging the pores and voids in the pulp matrix, this course of action can also decrease the overall strength of the composite material. Accordingly, the combination of strength-enhancing additives such as fibers or particles can be used to improve the overall strength of the composite material (i.e., coated fluff pulp), while the addition of the solvent prevents the polymer from blocking the pores in the matrix.

As a second step in the application process, prior to drying the coated cores, a crosslinker formulation can be introduced, advantageously comprising slow-diffusing crosslinking substances to ensure that crosslinking occurs predominantly at the surface of the polymeric coating. In embodiments, the crosslinker can be introduced into the polymeric mixture before it is applied to the fluff pulp matrix; in other embodiments, the crosslinker can be applied after the polymeric coating has been applied to the fluff pulp matrix.

Effective crosslinkers for creating a swellable connected polysaccharide network include citric acid, butanetetracarboxylic acid, poly(methyl vinyl ether-alt-maleic anhydride), polymeric methylene diphenyl isocyanate (PMDI), and any di- or multi-functional epoxide such as poly(ethylene glycol) diglycidyl ether, and the like. If epoxy crosslinkers are used, bases, tertiary ammonia, and quaternary ammonium catalysts can be added to reach appropriate crosslinking conversions. Depending on the source and grade of the polysaccharide used, varying amounts of crosslinker may be used. The crosslinking strategy for forming these absorbent fibrous composites is intended to minimize interior gel crosslinking, while restricting crosslinking to the surface of the polymeric coating. To accomplish this, a crosslinker can be selected that has flexible and extendible arms between crosslinking sites, so that the interior polymer chains within the polysaccharide coating can expand upon imbibition of liquid, allowing the coating matrix to retain liquid and swell.

An exemplary crosslinker formulation involves multifunctional epoxies with oligomeric arms. Such bulky crosslinkers are slow to diffuse, especially when there is a thick polymeric coating layer on the core prior to drying. This high viscosity layer results in reduced crosslinker diffusivity, which directs the reaction predominantly to the surface of the layer, while its interior remains unconstrained and uncrosslinked. An unconfined interior within the coating layer permits its facile expansion/swelling. Since the pulp-polymer complex is a core-shell configuration, gel particle shifting and clumping are no longer possible. The void space between fibers remain open, allowing rapid spreading of the absorbed liquid. As the liquid travels to distant portion of the absorbent matrix, it is absorbed evenly by the coated fibers. Further body-weight-induced distortion of the absorbent layer is borne by the intertwining fibrous matrix, where stress concentration is minimized. Thus, liquid extrusion from the liquid-swollen absorbent material is unlikely and preventable.

Examples of crosslinking agents include polyglycidyl ether compounds, haloepoxy compounds, polyaldehyde compounds, polyhydric alcohol compounds, polyamine compounds and polyisocyanate compounds. Multifunctional epoxides are particularly advantageous, for example, polyglycidyl ether compounds such as ethylene glycol diglycidyl ether, propylene glycol diglycidyl ether, glycerol-1,3-diglycidyl ether, glycerol triglycidyl ether, triglycidyl ethers of propxylated glycerin, polyethylene glycol diglycidyl ether and 1,6-hexanediol diglycidyl ether, and the like. Examples of haloepoxy compounds include epichlorohydrin and α-methyl epichlorohydrin. Examples of polyaldehyde compounds include glutaraldehyde and glyoxal. Examples of polyhydric alcohol compounds include glycerol, ethylene glycol, diethylene glycol, propylene glycol, polyethylene glycol, polypropylene glycol, diethanol amine and triethanol amine. Examples of polyamine compounds include ethylene diamine, diethylene triamine, triethylene tetramine, tetraethylene pentamine, polyamide resin as a reactant of polyamine and aliphatic polybasic acid and polyamide polyamine epichlorohydrin resin. Examples of polyisocyanate compounds include toluene diisocyanate, hexamethylene diisocyanate.

While crosslinking can be advantageous under certain circumstances, in certain cases crosslinking is unnecessary or undesirable. Crosslinking can be avoided entirely with some high-molecular weight swellable polymers because they are able to create on their own a highly entangled porous network, which permits greater swellability. Smaller molecular-weight molecules, however, are less likely to behave in this manner. Therefore, if smaller molecular-weight molecules swellable polymers are employed, crosslinking may be required; however, in embodiments, alternatives to crosslinking or supplements to crosslinking can be advantageous. In the latter case, adjuncts to crosslinking can improve performance and/or can decrease the amount of the crosslinking agent that is needed.

In embodiments, as an alternative or adjunct to crosslinking, smaller molecular-weight polymers can be intertwined with larger, more swellable polymers to create a highly entangled porous network, simulating the behavior of high molecular-weight polymers themselves. Such a heterogeneous polymer network can be produced by harnessing the phenomenon of charge-charge complexation: two dissimilar polymers having opposite charges can interact with each other to form an entangled porous network that can have useful swellability properties. In embodiments, a water-swellable coating layer for use with the composite materials disclosed herein can comprise a first and a second water-swellable polymer organized in a heterogenous polymer network formed via charge-charge complexation. In embodiments, a larger, highly branched swellable polymer can be used to form a "backbone" to which other, smaller, oppositely charged polymers can be attached; in other embodiments, smaller polymers can form a "backbone" with larger, oppositely charged polymers being attached; in yet other embodiments, the two oppositely charged polymers can be selected without regard for their size differences. In embodiments, two or more different, oppositely charged polymers can interact with each other to form an entangled network that permits greater swellability than a network formed from either polymer alone.

In an illustrative embodiment, a highly branched, charged, swellable polymer such as starch (cationic), can be used and mixed with an oppositely charged polymer such as CMC, alginate, pectin or the like (negatively charged). The branched cationic polymer and the smaller negatively charged components can then interact, forming a stable network. A plasticizer, as described previously (e.g., glycerin/glycerol), can be used with this charge-charge complexation network in order to enhance its absorption properties and otherwise improve performance. A small amount of any neutrally charged plasticizer, oligomer, or polymer can also be used with the charge-charge complexation network to improve performance, for example to prevent too much clumping or precipitation. In embodiments, a positively charged polymer can be used as the major component of the charge-charge complexation network or the main component supporting the network, and a negatively charged polymer can be used as the secondary component, to provide linkages and fill out the network. Alternatively, the negatively charged polymer can be used as the major or main component, with the positively charged secondary polymer creating the linkages. In embodiments, varied amounts of major and secondary polymers can be used, with the goal of providing enough of the major polymer to coat the fibers in the matrix to afford sites for attachment of the secondary linking polymer. In embodiments, ratios between about 50:50 of major polymer to secondary linking polymer can be used, up to ranges of about 90:10 to 95:5 of major polymer to secondary linking polymer. Advantageously, both polymers are highly swellable, although a less swellable secondary polymer can be used with a more swellable major component. In embodiments, more than two polymers can be used, with mixtures of positively-charged ones and negatively-charged ones.

As described above, a branched-chain polymer can be advantageously employed as backbone for charge-charge complexation networks. In other embodiments, a more linear polymer can be used in a similar way to support such a network. As an example, a small amount of positively charged polymer, such as chitosan, can be used as the main support for the complexation, with a larger amount of a smaller, negatively charged secondary polymer such as carboxymethylcellulose, alginate, pectin, or the like. A plasticizer such as glycerin/glycerol can be added to improve performance, for example by acting to lubricate and prop open the polymer chains and to permit more water uptake and/or to prevent clumping or precipitation. As used herein, the term glycerol refers to a pure form of glycerol, while glycerin refers to a formulation containing about 95% glycerol. A plasticizer such as glycerin exerts its advantageous effects due to the presence of glycerol in the glycerin; it is understood that using unadulterated glycerol as a plasticizer would be similarly advantageous.

In other embodiments, a negatively charged polymer can be used as the main support for the network, with larger amounts of smaller, positively charged polymers. Advantageously, all the polymers included in the charge-charge complexation network are swellable, but at least a major component or a main network support should be swellable. In embodiments, varying amounts of the main support polymer and the secondary polymer can be used, with either the major polymer or the secondary polymer having one charge with the other polymer having the opposite charge. As described previously for branched polymers, varied amounts of linear major and secondary polymers can be used, with the goal of providing enough of the major polymer to coat the fibers in the matrix to afford sites for attachment of the secondary linking polymer. In embodiments, ratios between about 50:50 of major polymer to secondary linking polymer can be used, up to ranges of about 90:10 to 95:5 of major polymer to secondary linking polymer. It is beneficial if all polymers used are swellable, with at least the main network support polymer being swellable. In embodiments, more than two polymers can be used, with mixtures of positively-charged ones and negatively-charged ones.

2. Methods of Manufacture

Manufacture of the absorbent fibrous composites can be accomplished using techniques familiar to those skilled in producing pulp products and absorbent articles. Many variations on these standard techniques can be employed as steps in the methods of manufacture. An exemplary description is provided herein to illustrate the principles of the invention.

In embodiments, the initial process for forming an absorbent article involves forming the cellulosic material coated with the superficially crosslinked water-swellable polymer, as disclosed herein. First, a fluff pulp or comparable cellulosic substrate is provided as a substrate in a dry or slightly wet form. This substrate can then be blended with a concentrated aqueous solution of the selected polymer(s), using standard industrial mixers, extruders, or the like, so that there is a substantially uniform layer of the water-swellable coating on the cellulosic fibers; alternatively, in other embodiments, an emulsion or other mixture of the selected water-swellable polymer(s) can be used instead of the concentrated aqueous solution.

Once appropriately coated with the water-swellable polymer solution, emulsion, or mixture, the resulting amalgam of coated fibers exits the blending equipment and undergoes sheet formation, using standard devices such as calendar rolls, blade coater post-mixing, or a slit die attached to the extruder. Following sheet formation, the selected crosslinker formulation is applied across the sheet via a spray bar or similar application tool. Even penetration of the crosslinker formulation throughout the sheet of coated cellulose is achieved through standard techniques, such as a pressure differential that pushes or pulls the crosslinker throughout the entire sheet. As a result, the external surfaces of the coating are exposed to crosslinker, and these water-swellable surfaces become crosslinked to each other while the water-swellable polymer underneath remains uncrosslinked. Drying by heat can affect the rate and extensiveness of crosslinking.

After the cellulosic material coated with the superficially crosslinked water-swellable polymer(s) is produced and is fashioned into a suitable form factor, it can be used to form absorbent articles. For use in a personal care product like a diaper or incontinence pad, the sheet can be subjected to gentle hammermilling to increase inter-fiber separation, thereby creating a high internal void fraction. For products formed using this technology, there is no need for fibers of the absorbent cellulosic material as disclosed herein to become fully disentangled, as would be required for the air-laying step in conventional absorbent article production. Instead, the hammermilled sheet of the cellulosic material coated with the superficially-crosslinked water-swellable polymer(s) can simply be die-cut to fit the desired contour of the absorbent article.

The methods for manufacturing absorbent articles using cellulosic material coated with the superficially-crosslinked water-swellable polymer(s) as disclosed herein offer several industrial advantages when compared to processes for manufacturing absorbent articles as currently practiced in the art. Importantly, the manufacturing processes disclosed herein are simpler than conventional ones, and less hammermilling is required. Thus, there is greatly decreased consumption of water and energy. The required equipment for manufacturing absorbent articles using cellulosic material coated with the superficially-crosslinked water-swellable polymer(s) is already available in the industry, and is expected to occupy an extremely compact footprint. The process yields a high-performance material for many absorbent applications, while involving low capital and operating expense.

In embodiments, articles incorporating the cellulosic material coated with the superficially-crosslinked water-swellable polymer(s) as disclosed herein can produce faster wicking (via longitudinal fluid spreading, i.e., along fiber axis) and higher fluid retention capacity (due to the prevalence of the water-swellable polymeric reservoir on all fibers). In addition, such products can exhibit increased wet strength, i.e., the water-swellable polymeric layer forms an extensive and continuous network across all pulp-pulp intersections, tethering the entire network together. Products manufactured to incorporate cellulosic materials coated with the superficially-crosslinked water-swellable polymer(s) can be engineered to optimize their performance features, including highly customizable and tunable absorption capacity, softness, requisite fiber density, wide-ranging pulp type and pulp mix, optimizable sheet thickness, and the like. Such materials can be employed in a variety of form factors, including structures like paper towels where thinness is desired.

Absorbent articles manufactured from cellulosic materials coated with the superficially-crosslinked water-swellable polymer(s) as disclosed herein can be combined with other additives and technologies to create a range of useful products via materials embedded in or attached to the polymer layer. For example, additives for personal care articles incorporated into the polymer layer can include plasticizers (e.g., glycerin, PEG, Pluronics, and the like) to impart product softness and superior hand-feel. As another example, skin rejuvenating ingredients (e.g., hyaluronic acid, aloe vera, alpha-lipoic acid, and vitamins C&E) can be loaded in the polymer layer. Medication (e.g., hydrocortisone, anti-fungal agents) can be incorporated into the polymer layer to produce medicated articles, for example to treat diaper rash or other skin conditions. In other embodiments, wound dressings can be prepared using the absorbent fibrous composites disclosed herein, with additional medications being included in the polymer layer, such as antiseptics, anti-microbial agents, blood clotting agents, and the like. Odor-absorbing or odor-neutralizing chemicals (e.g., beta-cyclodextrin, bicarbonate, pentane-1,5 diol, etc.), scents, fragrances, and other odorant modifiers can be advantageously introduced into or onto this layer.

3. Exemplary Articles
A. Personal Care Items

A variety of personal care articles can be formed using the cellulosic materials coated with the superficially-crosslinked water-swellable polymer(s), as disclosed herein. Diapers, incontinence pads, feminine hygiene products, and the like, can be formed more economically, and worn more conveniently and comfortably. In addition, the performance of these traditional articles can be improved, for example with better moisture wicking and breathability.

Traditional absorbent articles can further be modified to take advantage of the high-performance properties of the disclosed cellulosic materials coated with the superficially-crosslinked water-swellable polymer(s). For example, diaper construction can be modified to include a reusable external covering and a disposable internal component. In an embodiment, this construction comprises a reusable (semi-permanent) elastic mesh and a (used-once) disposable integrated structure. The external mesh can be constructed to conform to the wearer's body contours, and can be made of durable elastic material (e.g., Lycra, Spandex, silicone, etc.). This mesh architecture for the external covering is porous, thus highly breathable. The elastic mesh is used to confine an absorbent interior structure comprising several layers: (a) closest to the skin, a slightly debonded absorbent cellulosic material layer as described herein; (b) external to that layer, an optional layer of hydrophobically treated fluff pulp; and (c) external to that layer, an optional porous paper layer that provides a backing for the fluff pulp layers. This multi-layered absorbent interior core structure can be changed/replaced when it is soiled, while the reusable mesh layer remains in place. Besides the convenience of this approach, it can reduce skin contact time with excretions, and mitigate resulting skin irritation problems like diaper rash.

This approach to diaper construction, using replaceable diaper inserts analogous to changeable filters for coffee machines or vacuum cleaners, is already familiar to the consumer, and offers distinct price and environmental advantages since only a small portion of the overall diaper requires disposal. By using biodegradable materials in the absorptive core instead of traditional synthetic SAPs, the absorbent cellulosic material-based product is intrinsically less environmentally burdensome. By providing a smaller sized absorbent core for disposal, as compared to the traditional form factor for a disposable diaper, the absorbent cellulosic material-based product is suitable for small-scale composting instead of large-scale disposal facilities. Overall, this approach can enable environmentally sustainable reimagination of the whole disposable diaper industry.

b. Freezer Packs

In embodiments, the cellulosic materials coated with the superficially-crosslinked water-swellable polymer(s) disclosed herein can be used to form other useful articles where liquid absorption and retention is important, besides personal care articles. For example, a multilayered structure similar to the one described above for replaceable diaper inserts can be shaped to form an article useful as a freezer pack. In embodiments, such a product can comprise two functional layers, one layer of a cellulosic material coated with superficially-crosslinked water-swellable polymer(s), and one layer of a hydrophobically treated fluff pulp: the former is liquid-absorbing and the latter is liquid-repelling. If the liquid-repelling layer surrounds the entire liquid-absorbing core, then the construction can be used as a high-performance freezer pack, where the liquid-absorbing layer is pre-loaded with water or glycerol-water mixture (or similar liquid compositions that are known to freeze below zero centigrade, to provide sub-zero cryogenic control). The water-repelling layer all around the liquid-filled core ensures that even upon thawing, the package stays dry to the touch. An outermost paper layer can provide mechanical protection of the entire assembly. The construct is low-cost to manufacture and readily disposable.

EXAMPLES

Materials and equipment used in Examples 1-4 include:
NBSK fluffed pulp: Performance BioFilaments
ERISYS GE-36: CVC Thermoset Specialties (triglycidyl ether of propoxylated glycerin)
Xanthan Gum (food grade—Bob's Red Mill): Amazon
Sigma Aldrich Chemicals
    Pectin from citrus peel
    Amylopectin from maize
    Sodium carboxymethyl cellulose
    Benzyltrimethylammonium chloride
    1-Butanol
    Glycerol
Corning stir/hot plate
BINDER forced convection oven Example 1: Crosslinked Hydrocolloid (Pectin) Coated Pulp Methods: 4 g of northern bleached softwood kraft (NBSK) pulp was evenly dispersed in 1 L of tap water using a magnetic stir plate. The dispersion was then filtered over a Buchner funnel containing a 40-mesh screen to isolate the hydrated pulp fibers. 8 g of 1% pectin aqueous solution was then thoroughly hand-mixed with the wet pulp using a spatula. 1.6 g of 0.1% crosslinking solution (ERYSIS GE-36: trifunctional epoxide crosslinker in 1-butanol) and 1.6 g of 0.05% catalyst solution (benzyltrimethylammonium chloride in deionized (DI) water) were added and hand-mixed with the coated pulp fibers in subsequent steps. The resulting mass was spread over a baking sheet and dried at 110° C. for three hours in a BINDER forced convection oven.

Absorption test: The resulting dried sheet of coated pulp fibers was cut into smaller pieces to test samples in triplicate. Each test was initiated by recording the weight of the dry pulp sample. The pulp sheet was evenly hydrated drop by drop with tap water using a 3 mL pipette. The pulp sheet was carefully lifted with tweezers between intermittent steps of water addition (1-5 droplets) to check for signs of fiber saturation. Upon the onset of saturation, any water added to the fibers was deposited on the plastic weigh boat below the sheet. When this was first observed, the weight of the saturated sheet was taken, and the absorption capacity of the sample was calculated according to Equation 1 below:

$$\text{Water Absorption Capacity} = \frac{\text{saturated } pulp\,weight - \text{dry pulp weight}}{\text{dry pulp weight}} \quad \text{EQ. 1}$$

A control sample was prepared for performance comparison following the same dispersion, filtering, and drying methods detailed above, but without the inclusion of the crosslinked hydrocolloid coating material.

Example 2: Crosslinked Hydrocolloid (Carboxymethyl Cellulose) Coated Pulp

The same procedures, chemical quantities, and equipment as Example 1 were followed to produce a NBSK pulp sample coated with carboxymethyl cellulose (CMC) rather than pectin. The same testing protocol was also followed to assess the absorption capacity as Example 1.

Example 3: Crosslinked Hydrocolloid (Xanthan Gum) Coated Pulp

The same procedures, chemical quantities, and equipment as Example 1 were followed to produce a NBSK pulp sample coated with xanthan gum rather than pectin. The same testing protocol was also followed to assess the absorption capacity as Example 1.

Example 4: Crosslinked Hydrocolloid (Amylopectin) Coated Pulp

The same procedures, chemical quantities, and equipment as Example 1 were followed to produce a NBSK sample coated with amylopectin rather than pectin. The same testing protocol was also followed to assess the absorption capacity as Example 1.

A summary of the average absorption capacity of Examples 1-4 is presented in Table 1.

TABLE 1

| Average Water Absorption Capacity of Hydrocolloid Coated Pulp Fibers | |
|---|---|
| Example | Water Absorption Capacity |
| 1 | 6.6 ± 0.1 |
| 2 | 6.4 ± 0.2 |
| 3 | 7.0 ± 0.2 |
| 4 | 6.1 ± 0.1 |
| Control | 5.5 ± 0.4 |

Example 5: Crosslinked Hydrocolloid with Plasticizer Coated Pulp

A NKSB pulp sample coated with xanthan gum was produced following procedures similar to those in Example 3. However, the 8 g of 1% xanthan gum aqueous solution also included 0.1% glycerol as an added plasticizer prior to mixing with the filtered pulp fibers. The 8 gm of xanthan gum aqueous solution contained 7.912 g DI water, 0.08 g XG, and 0.008 g glycerol. The same absorption testing protocols were followed and revealed similar results as Example 3: 6.9±0.2. While water uptake capacity was not significantly impacted by the addition of a plasticizer, the dried pulp sheet, upon inspection, was observed to be far more malleable than any of the previous samples.

Examples 6 and 7

Materials and equipment used in Examples 6-7 include:
Walnut husk granules (Amazon)
*Psyllium* husk powder (Amazon)
Fluff pulp
70 mesh filter
Buchner funnel
Graduated cylinder
Calcium chloride (Sigma Aldrich)
Sodium Alginate (Sigma Aldrich)
DI Water
Sodium Chloride

Example 6: *Psyllium* Husk Powder Additive

Very fine *psyllium* husk powder was added to a swellable fluff pulp matrix to determine whether or not strengthening, or increased swelling, would occur. Eight grams of fluff pulp was weighed out into a beaker with 1 L of DI water and was mixed up on a stir plate for about 15 minutes to distribute the pulp. Separately, a 1% stock solution of sodium alginate was made by aggressively mixing 1 g of sodium alginate with 99 grams of 0.1% glycerol in DI water for about 15 minutes, and then slowly mixing the solution until everything was dissolved and the solution was homogeneous. The pulp slurry was filtered through a 70-mesh screen until clear water was seen and all pulp sat on top of the filter, forming a filter cake. The final filter cake was weighed (65.62 g). Four samples were made from the filter cake, so about 16.46 g was weighed out into each of four different beakers. It was assumed that each of the four beakers contained 2 g of original 8 g of dried pulp, and a 3% swellable coating add on (based on dry pulp) was added to each beaker. This was done by adding 6 g of the 1% alginate solution to each of the four beakers and mixing thoroughly with a spatula. The four beakers for testing would contain two samples each of 25% and two samples each of 50% of the *psyllium* husk powder (based on dry pulp weight), so walnut granules were added to the four beakers and mixed in thoroughly with a spatula. For crosslinking purposes, a 0.5% solution of calcium chloride was made up, and 0.6 g of it was added to each of the four beakers, and mixed in thoroughly with a spatula. Each of the four mixtures was spooned into a silicone mold and put in the oven to dry overnight at 70° C. Samples were weighed and tested with a 1-minute submersion in 0.9% sodium chloride solution and subsequent 1 minute air dry before being weighed again to determine swelling capacity. Qualitatively, each sample was pulled apart by hand to determine any increased strength. Increased strength was determined by a "yes" or "no" based on whether it took more force to pull apart than a control sample. The "Swell X" is a multiple of the original dry weight, which is determined by subtracting the dry weight from the wet weight, and dividing by the dry weight. Results for Example 5 and Example 6 are set forth in Table 2 below.

Example 7: Walnut Husk Granules Additive

Walnut husk granules were added to a swellable fluff pulp matrix to determine whether or not strengthening, or increased swelling, would occur. The walnut husk was in a granular form, larger than the *psyllium* husk powder in the previous experiment. Twelve grams of fluff pulp was weighed out into a beaker with 1.5 L of DI water and was mixed up on a stir plate for about 15 minutes to distribute the pulp. Separately, a 1% stock solution of sodium alginate was made by aggressively mixing 1 g of sodium alginate with 99 grams of 0.1% glycerol in DI water for about 15 minutes, and then slowly mixing the solution until everything was dissolved and the solution was homogeneous. The pulp slurry was filtered through a 70-mesh screen until clear water was seen and all pulp sat on top of the filter, forming a filter cake. The final filter cake was weighed (97.61 g). Six samples were made from the filter cake, so about 16.27 g was weighed out into each of six different beakers. It was assumed that each of the six beakers contained 2 g of original 12 g of dried pulp, and a 3% swellable coating add on (based on dry pulp) was added to each beaker. This was done by adding 6 g of the 1% alginate solution to each of the six beakers and mixing thoroughly with a spatula. The six beakers for testing would contain 0% (control), 1%, 5%, 10%, 25%, and 50% of the walnut granules (based on dry pulp weight), so walnut granules were added to the six beakers in the amounts of 0 g (control), 0.02 g, 0.1 g, 0.2 g, 0.5 g, and 1 g and mixed in thoroughly with a spatula. For crosslinking purposes, a 0.5% solution of calcium chloride was made up, and 0.6 g of it was added to each of the six beakers, and mixed in thoroughly with a spatula. Each of the 6 mixtures was spooned into a silicone mold and put in the oven to dry overnight at 70° C. Samples were weighed and tested with a 1-minute submersion in 0.9% sodium chloride solution and subsequent 1 minute air dry before being weighed again to determine swelling capacity. Qualitatively, each sample was pulled apart by hand to determine any increased strength. Increased strength was determined by a "yes" or "no" based on whether it took more force to pull apart than a control sample. The "Swell X" is a multiple of the original dry weight, which is determined by subtracting the dry weight from the wet weight, and dividing by the dry weight. Results for Example 6 are set forth in Table 2 below.

TABLE 2

Strength Testing with Additives

| Sample | Dry Weight | Wet Weight | Swell | Increased Strength Compared to Control? |
|---|---|---|---|---|
| 0% Control | 1.99 | 14.36 | 6.2X | N/A |
| 1% Walnut | 2.14 | 14.75 | 5.9X | No |
| 5% Walnut | 2.02 | 14.09 | 6.0X | No |
| 10% Walnut | 2.14 | 14.53 | 5.8X | No |
| 25% Walnut | 2.35 | 15.03 | 5.4X | No |
| 50% Walnut | 3.06 | 17.08 | 4.6X | No |
| 25% Psyllium | 2.59 | 14.30 | 4.5X | Yes |
| 50% Psyllium | 4.45 | 12.05 | 1.7X | Yes |

Example 8: Fluff Pulp Complexation

Materials
Sigma Aldrich Chemicals
    Hydroxyethyl Cellulose (HEC)
    Acetic Acid
    Chitosan
    Sodium Carboxymethyl Cellulose (CMC)
    Glycerol
    1-Butanol
Other
    Caprylyl Glucoside (CG): Cocojojo Organics
    ERISYS GE-36: Huntsman Chemical
    Northern Bleached Softwood Kraft Pulp: Performance BioFilaments
Equipment
    Corning stir plate
    BINDER forced convection oven Methods: In this Example, three samples were composed in triplicate for comparison of water absorption capacity. First, 18 g of NBSK pulp was mixed in 2 L DI water on a stir plate until thoroughly dispersed. The suspension was subsequently filtered through a Buchner funnel containing a 40-mesh screen. The resulting wet pulp was divided into three equal parts (control, treatment sample 1, treatment sample 2). A 0.5 wt % crosslinking solution was prepared for both treatment samples by dissolving 0.025 g ERISYS GE-36 in 4.975 g 1-butanol. The 1.1 wt % swellable polymer solution for treatment 1 was prepared by dissolving 0.125 g HEC, 0.375 g CG, and 0.05 g glycerol in 49.45 g DI water. Two separate solutions were prepared for treatment 2: the cationic solution consisted of 1 wt % chitosan dissolved in a 1 wt % acetic acid solution (i.e., 0.1 g chitosan, 0.1 g acetic acid, and 9.8 g water) while the 1.1 wt % anionic solution consisted of 0.0625 g CMC, 0.0625 g HEC, 0.375 g CG, and 0.05 g glycerol dissolved in 49.45 g DI water. Sample 1 was coated by mixing 18 g of 1.1 wt % treatment 1 solution in a beaker using a spatula. 0.9 g of 0.5 wt % crosslinking solution was then added and mixed before depositing the final mixture into three wells of a 1"×1" silicone cube tray. Sample 2 was coated with 6 g of cationic solution, then briefly dried at 90° C. for 10 min in the oven. The semi-dry pulp was then coated with 18 g of anionic solution, followed by 0.9 g of 0.5 wt % crosslinking solution. The resulting mixture was similarly placed in three wells of the cube tray. Lastly, 18.9 g of DI water was mixed into the control pulp beaker (for comparable solids content to treatment samples) and dispensed into three wells of the cube tray. All samples were dried at 90° C. for 8 hr in the oven.

Absorption test: Every absorption test was initiated by measuring the weight of the dry sample. The sample was placed inside a metallic mesh cage and completely submerged in DI water using an 80 mL beaker. After soaking for 1 min, the cage was removed from the beaker and the sample dripped excess water for 1 min before measuring the wet weight. Absorption capacity was calculated by using EQ 1, as set forth in Example 1 above. A summary of the absorption performance of all three samples is presented in Table 3 below.

TABLE 3

Average Water Absorption Capacity of Coated NBSK Pulp

| Sample | Avg Absorption Capacity |
|---|---|
| Control | 6.1 ± 0.2 |
| Treatment 1 | 6.5 ± 0.1 |
| Treatment 2 | 7.2 ± 0.1 |

While this invention has been particularly shown and described with references to preferred embodiments thereof, it will be understood by those skilled in the art that various changes in form and details may be made therein without departing from the scope of the invention encompassed by the appended claims. Many variations of the invention will become apparent to those of skilled art upon review of this specification. Unless otherwise indicated, all numbers expressing reaction conditions, quantities of ingredients, and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

The invention claimed is:

1. A composite material, comprising a fluff pulp fiber that is at least partially coated by a water-swellable coating layer, wherein the water-swellable coating layer comprises a first water-swellable polymer and a second water-swellable polymer, wherein the first water-swellable polymer is a carboxyalkyl cellulose and the second water-swellable polymer is xanthan gum.

2. The composite material of claim 1, wherein the first water-swellable polymer and the second water-swellable polymer are organized in a heterogenous polymer network formed by charge-charge complexation.

3. The composite material of claim 1, wherein the water-swellable coating layer comprises a foam.

4. The composite material of claim 3, wherein the foam is sustained or formed by a foam-producing material.

5. The composite material of claim 4, wherein the foam-producing material comprises a surfactant.

6. The composite material of claim 1, wherein the water-swellable coating layer comprises one or more additives not having water-swellable properties.

7. The composite material of claim 6, wherein at least one of the one or more additives is selected from the group consisting of plasticizers, skin rejuvenating agents, medications, odor absorbers or neutralizers, and fragrances.

8. The composite material of claim 1, wherein the carboxyalkyl cellulose is selected from the group consisting of carboxymethylcellulose, hydroxyethyl cellulose, and carboxymethyl hydroxyethyl cellulose.

9. The composite material of claim 1, wherein the first water-swellable polymer and the second water-swellable polymer forms a hydrogel upon contact with water.

10. The composite material of claim 1, wherein the water-swellable polymer layer is crosslinked.

11. The composite material of claim 10, wherein the water-swellable polymer layer is crosslinked only on its surface.

12. An article of manufacture comprising the composite material of claim 1.

13. The article of manufacture of claim 12, wherein the article is a personal care product.

14. A method of manufacturing the composite material of claim 1, comprising:
providing the fluff pulp fiber in dry or wet form;
mixing the fluff pulp fiber with an aqueous suspension of the first water-swellable polymer and the second water-swellable polymer to form a coating mixture;
applying the coating mixture to the fluff pulp fiber to form a coated fluff pulp fiber having a substantially uniform coating; and
forming the coated fluff pulp fiber into a sheet.

15. A method of forming an absorbent article, comprising:
i) treating the composite material of claim 1 with a mechanical separation process to increase interfiber separation;
ii) drying the composite material before or after the step i, thereby forming a dried absorbent fibrous product; and
iii) cutting the dried absorbent fibrous product into a shape suitable for the absorbent article.

\* \* \* \* \*